(12) United States Patent
Kim et al.

(10) Patent No.: US 8,759,587 B2
(45) Date of Patent: *Jun. 24, 2014

(54) METHOD FOR PREPARATION OF 4,4'-DINITRODIPHENYLAMINE AND 4,4'-BIS(ALKYLAMINO)DIPHENYLAMINE BY USING 4-NITROANILINE

(75) Inventors: Jin-Eok Kim, Daejeon (KR); Seoung-Il Kim, Daejeon (KR); Han Jin Kwag, Daejeon (KR); Sang hee Park, Daejeon (KR)

(73) Assignee: Korea Kumho Petrochemical Co., Ltd. (KR)

( * ) Notice: Subject to any disclaimer, the term of this patent is extended or adjusted under 35 U.S.C. 154(b) by 48 days.

This patent is subject to a terminal disclaimer.

(21) Appl. No.: 13/162,618

(22) Filed: Jun. 17, 2011

(65) Prior Publication Data

US 2012/0157714 A1 Jun. 21, 2012

(30) Foreign Application Priority Data

Dec. 21, 2010 (KR) .................... 10-2010-0131740

(51) Int. Cl.
  *C07C 209/00* (2006.01)
(52) U.S. Cl.
  USPC .......................... 564/414; 564/415
(58) Field of Classification Search
  None
  See application file for complete search history.

(56) References Cited

U.S. PATENT DOCUMENTS

| 4,990,673 | A | 2/1991 | Tronich et al. |
| 5,117,063 | A | 5/1992 | Stern et al. |
| 5,252,737 | A | 10/1993 | Stern et al. |
| 5,331,099 | A | 7/1994 | Stern et al. |
| 5,380,407 | A | 1/1995 | Yamaoka et al. |
| 5,436,371 | A | 7/1995 | Stern et al. |
| 5,453,541 | A | 9/1995 | Stern et al. |
| 5,552,531 | A | 9/1996 | Stern et al. |
| 5,633,407 | A | 5/1997 | Stern et al. |
| 6,156,932 | A * | 12/2000 | Joo et al. ................ 564/414 |
| 6,198,001 | B1 * | 3/2001 | Joo et al. ................ 564/414 |
| 6,245,943 | B1 * | 6/2001 | Joo et al. ................ 564/423 |
| 2012/0157713 | A1 * | 6/2012 | Kim et al. ................ 564/414 |
| 2012/0197044 | A1 * | 8/2012 | Kim et al. ................ 564/420 |

FOREIGN PATENT DOCUMENTS

| CN | 101717339 | 6/2010 |
| GB | 1091376 | 11/1967 |
| JP | 10-168038 | 6/1998 |
| JP | 10-219243 | 8/1998 |
| KR | 10-2001-0054045 | 7/2001 |
| KR | 10-0334490 | 4/2002 |
| WO | 9324447 | 12/1993 |

OTHER PUBLICATIONS

Krylova et al., "Vicarious C-Amination of Nitrobenzene", Russian Journal of Organic Chemistry, vol. 37, No. 6, 2001, pp. 887-888.
Iida et al., "The Reactions of p-Nitroaniline with Nitrobenzene Derivatives in Strongly Basic Solution," Journal of the Japanese Chemical Society, (1) pp. 138-143, (1976), with English Language Abstract.
Krylova, O.V., et al., "Vicarious C-Amination of Nitrobenzene",Russian Journal of Organic Chemistry, vol. 37(6), pp. 887-888 (2001). (2 pages total).

* cited by examiner

*Primary Examiner* — Clinton Brooks
(74) *Attorney, Agent, or Firm* — Stuart H. Mayer; Mayer & Williams, PC

(57) ABSTRACT

Provided is a method of preparing 4,4'-dinitrodiphenylamine (4,4'-DNDPA) in high yield by reacting 4-nitroaniline with excess nitrobenzene via the NASH reaction, and a method of preparing 4,4'-bis(alkylamino)diphenylamine (4,4'BAADA) in high yield and purity by hydrogenating the resulting 4,4'-DNDPA with a ketone compound in the presence of hydrogen and hydrogenation catalyst. The disclosed process is simple, allows selective preparation of 4,4'-DNDPA without byproducts, and thus allows preparation of 4,4'-BAADA in high yield without a complicated purification procedure.

18 Claims, No Drawings

METHOD FOR PREPARATION OF 4,4'-DINITRODIPHENYLAMINE AND 4,4'-BIS(ALKYLAMINO)DIPHENYLAMINE BY USING 4-NITROANILINE

CROSS-REFERENCE TO RELATED APPLICATIONS

This application claims priority under 35 U.S.C. §119 to Korean Patent Application No. 10-2010-0131740, filed on Dec. 21, 2010, in the Korean Intellectual Property Office, the disclosure of which is incorporated herein by reference in its entirety.

BACKGROUND (a) Technical Field

The present invention relates to a method for preparation of 4,4'-dinitrodiphenylamine and 4,4'-bis(alkylamino)diphenylamine.

(b) Background Art 4,4'-Dinitrodiphenylamine (4,4'-DNDPA) is easily reduced to 4,4'-diaminodiphenylamine (4,4'-DADPA) and is used as a source of an antioxidant in dyes and rubbers. Japanese Patent Application Publication No. H10-168038 discloses synthesis of 4,4'-DADPA by reducing 4,4'-DNDPA and describes that the 4,4'-DADPA compounds are excellent intermediates of additives for preventing oxidation and aging. As such, 4,4'-DADPA or 4,4'-DADPA derivatives are used as intermediates for additives of rubbers as well as dyes, agrichemicals and pharmaceuticals.

As a method of preparing 4,4'-DNDPA, nitration of N-acetyldiphenylamine followed by deacetylation is known. However, this method is problematic in that the nitration does not occur uniformly and separation by repeated recrystallization in alcohol is required. As another method, U.S. Pat. No. 4,990,673 discloses preparation of 4,4'-DNDPA by reacting 4-chloroaniline with an alkali metal cyanate. However, this method is problematic in that the reaction should be performed at 160° C. or above for at least 15 hours.

Also, a method of preparing DNDPA derivatives by reacting 4-nitroaniline (4-NA) with nitrobenzene derivatives is known [Bull. Chem. Soc. Jap., 1976, (1), p. 138-143]. In the reaction of 4-NA with the nitrobenzene derivative, a base such as potassium t-butoxide (t-BuOK) is used. Although it is described that ortho- and para-hydrogen-substituted and halogen-substituted products such as 2,4'-DNDPA, 4,4'-DNDPA, 5-chloro(bromo)-2,4'-dintrodiphenylamin, etc. are prepared depending on the used base amount, the process of preparing 4-NA is required and it is not easy to prepare 4,4'-DNDPA selectively.

As a method of reacting 4,4'-DADPA with ketones, Great Britain Patent No. 1091376 describes a method of reacting 4,4'-DADPA with ketones to prepare 4-amino-4'-alkylamino-diphenylamines at high temperature and high pressure in the presence of a precious metal catalyst, and Japanese Patent Application Publication No. H10-219243 describes reaction of 4,4'-DADPA with ketones to prepare 4,4'-bis(alkylamino) diphenylamine (4,4'-BAADA). However, 4,4'-DNDPA must be converted to 4,4'-DADPA before reaction with ketones and it is not easy to prepare pure 4,4'-DADPA.

The recently known nucleophilic aromatic substitution for hydrogen (NASH) reaction is advantageous in that harmful substances or difficult-to-remove intermediates are not generated since amines or amides are directly reacted with nitrobenzene or nitrobenzene derivatives in the presence of a base catalyst.

A method of directly reacting aniline and nitrobenzene in the presence of a base such as tetramethylammonium hydroxide (TMAH) to prepare 4-nitrodiphenylamine (4-NDPA), 4-nitrosodiphenylamine, etc. is known [J. Am. Chem. Soc., 1992, 114(23), 9237-8, U.S. Pat. Nos. 5,117,063, 5,252,737, 5,331,099, 5,453,541, 5,552,531, 5,633,407].

And, U.S. Pat. Nos. 5,436,371, 5,380,407 and PCT Application Publication No. WO 93/24447 describe a method of synthesizing N-(4-nitrophenyl)benzamide by the NASH reaction using benzamide instead of aniline. It is described that nitrobenzene and benzamide are used at a molar ratio of about 1:1 to synthesize N-(4-nitrophenyl)benzamide, and then 4-NA is prepared therefrom by hydrolysis using water or ammonia. However, production of 4,4'-DNDPA is not mentioned in these patents, because the N-(4-nitrophenyl)benzamide resulting from the reaction of benzamide with nitrobenzene is stable and separable, and does not react further with nitrobenzene.

SUMMARY

The inventors of the present invention have worked to solve the aforesaid problems. As a result, they have developed a method of preparing 4,4'-dinitrodiphenylamine (4,4'-DNDPA) selectively in high yield by reacting 4-nitroaniline with excess nitrobenzene via the NASH reaction, and hydrogenating the 4,4'-DNDPA with a ketone compound in the presence of hydrogen and a hydrogenation catalyst to prepare 4,4'-bis(alkylamino)diphenylamine (4,4'-BAADA) in high yield and purity.

Accordingly, the present invention is directed to providing a method for selectively preparing 4,4'-DNDPA from inexpensive source materials via a simple process without byproducts and thus preparing 4,4'-BAADA in high yield without a complicated purification process.

In one general aspect, the present invention provides a method for preparing 4,4'-dinitrodiphenylamine by reacting 4-nitroaniline with nitrobenzene in a polar organic solvent in the presence of a base.

In another general aspect, the present invention provides a method for preparing 4,4'-bis(alkylamino)diphenylamine (the alkyl is $C_1$-$C_{18}$ alkyl) including:

(1) reacting 4-nitroaniline with nitrobenzene in a polar organic solvent in the presence of a base to prepare 4,4'-dinitrodiphenylamine; and (2) hydrogenating the resulting 4,4'-dinitrodiphenylamine with a ketone compound in the presence of a hydrogenation catalyst to prepare 4,4'-bis(alkylamino)diphenylamine.

The above and other aspects and features of the present invention will be described infra.

DETAILED DESCRIPTION

Hereinafter, reference will now be made in detail to various embodiments of the present invention, examples of which are illustrated in the accompanying drawings and described below. While the disclosure will be described in conjunction with exemplary embodiments, it will be understood that the present description is not intended to limit the disclosure to those exemplary embodiments. On the contrary, the disclosure is intended to cover not only the exemplary embodiments, but also various alternatives, modifications, equivalents and other embodiments, which may be included within the spirit and scope of the disclosure as defined by the appended claims.

The present invention relates to a method for preparing 4,4'-dinitrodiphenylamine (4,4'-DNDPA) by reacting 4-nitroaniline with nitrobenzene in a polar organic solvent in the presence of a base catalyst, and a method for preparing 4,4'-bis(alkylamino)diphenylamine (4,4'-BAADA) by hydrogenating the resulting 4,4'-DNDPA with a ketone compound in the presence of a hydrogenation catalyst.

First, a method of reacting 4-nitroaniline with nitrobenzene in a polar organic solvent in the presence of a base to prepare 4,4'-DNDPA will be described.

In the reaction, a polar organic solvent such as dimethyl sulfoxide (DMSO), dimethylformamide, N-methylpyrrolidinone, etc. is used in consideration of the solubility of the urea and the base. Specifically, the reactants (4-nitroaniline and nitrobenzene) and the polar organic solvent may be used at a ratio of 1:1-50, more specifically 1:1-30, based on volume.

The reactants, i.e. the 4-nitroaniline and the nitrobenzene, may be used at a molar ratio of 1:1-16, more specifically 1:1-8, when considering yield.

The base may be an alkali metal base, an alkaline earth metal base or an organic amine base. Specifically, one or more selected from the group consisting of sodium hydroxide (NaOH), potassium hydroxide (KOH), potassium t-butoxide (t-BuOK) and tetramethylammonium hydroxide (TMAH) or a catalyst complex thereof with a bis-quaternary ammonium base may be used. The bis-quaternary ammonium base is represented by Chemical Formula 1, wherein $R_1$ and $R_2$ are independently $C_1$-$C_{18}$ alkyl, specifically one selected from methyl, n-propyl, isopropyl, allyl, butyl or dodecyl; $R_3$, $R_4$, $R_5$ and $R_6$ are independently $C_1$-$C_6$ linear or branched alkyl, specifically one selected from methyl, ethyl, n-propyl or isopropyl; and $R_7$ is $C_2$-$C_6$ alkylene or $C_2$-$C_6$ alkylene substituted with alcohol, specifically one selected from ethylidene, propylidene, 2-methoxypropylidene, 2-ethoxypropylidene or butylidene.

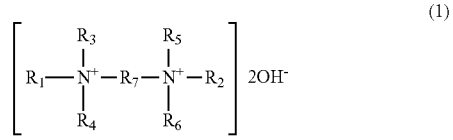

(1)

Specifically, the 4-nitroaniline and the base catalyst complex are used at a molar ratio 1:1-20, more specifically 1:1-6. If the base catalyst is used in a smaller amount, 4-nitroaniline may remain.

The reaction for preparing the 4,4'-DNDPA is performed under oxygen, air or nitrogen atmosphere at room temperature (20° C.) to 100° C., more specifically at 50-80° C. If the reaction temperature is too low, the reaction proceeds too slowly. And, if it is too high, reaction yield may decrease greatly because of decomposition of unwanted side reaction. At lower reaction temperatures, it requires a long time for 4-nitroaniline to be converted to 4,4'-DNDPA, but the reaction yield may be improved by increasing reaction time. In contrast, at higher reaction temperatures, although the initial yield is high, the final yield may decrease due to the side reaction. Thus, the reaction yield may be improved by selecting an adequate temperature capable of increasing the reaction rate while preventing the side reaction.

Unlike general NASH reactions, the reactivity is not greatly affected even when the water content is less than 5% of the total reaction solution by weight. Thus, it is not necessary to use a special process for removing water from the solvent. When water is added in an amount of about 1% of the solvent by weight, the initial yield is high but the yield at about 6 hours is not so high as compared to when water is not added. When the reaction is performed in the absence of oxygen, excess azoxybenzene is produced, unlike under oxygen atmosphere.

After the reaction is completed, the base catalyst may be removed by filtering and the reaction solvent may be separated by distillation for reuse. For separation and purification, the produced 4,4'-DNDPA is added to water or an acidic aqueous solution, refluxed after adding a nonpolar organic solvent, and then solidified by cooling. The amount of the water or the acidic aqueous solution may be 3-7 times (based on weight), and the amount of the nonpolar organic solvent may be 1-5 times (based on weight) of the product. If the nonpolar organic solvent is used excessively, the yield may decrease due to poor solubility. On the contrary, if it is used too little, it is not easy to remove the solvent and byproducts. Specifically, the nonpolar organic solvent may be toluene, hexane, cyclohexane, etc. Through the separation and purification, high-purity 4,4'-DNDPA is obtained, which can be used to prepare 4,4'-BAADA without further purification.

Next, the prepared 4,4'-DNDPA is hydrogenated with a ketone compound in the presence of a hydrogenation catalyst to prepare 4,4'-BAADA.

The hydrogenation catalyst may be a precious metal catalyst such as Pd or Pt, or a reduction catalyst such as Ni—Fe—Al, Cu—Cr, Raney Ni, etc. Especially, a carbon-supported precious metal catalyst such as Pt/C or Pd/C may be used. The hydrogenation catalyst may be used in an amount of 0.05-0.2 part by weight per 1 part of the 4,4'-DNDPA by weight. If the amount of the hydrogenation catalyst is too small, yield may be low. On the contrary, if the amount is too large, the process becomes uneconomical.

The ketone compound may be an alkylketone or a cycloalkylketone. The alkylketone may be a $C_1$-$C_{10}$ alkylketone and may be specifically acetone, methyl isobutyl ketone (MIBK), methyl isoamyl ketone, methyl ethyl ketone, methyl n-butyl ketone, etc. The cycloalkylketone may be a $C_1$-$C_{10}$ cycloalkylketone and may be specifically cyclohexanone, methyl cyclohexyl ketone, etc. The ketone serves both as reactant and solvent and may be used in an excess amount of 3-10 mol per 1 mol of the 4,4'-DNDPA.

The reaction rate of the hydrogenation reaction (step (2) reaction) is dependent on reaction temperature and hydrogen pressure. In general, the reaction proceeds efficiently at a hydrogen pressure or 300-1000 psi and a reaction temperature of 50-200° C.

After the reaction is completed, the ketone compound is removed by distillation and 4,4'-BAADA is obtained.

When used as an antiaging agent of a tire rubber comprising natural or synthetic rubber, the 4,4'-BAADA prepared in accordance with the present invention exhibits 10-30% improved antiaging performance as compared to the currently commercially available N-(1,3-dimethylbutyl)-N'-phenyl-p-phenylenediamine (6PPD).

Accordingly, the 4,4'-BAADA prepared in accordance with the present invention may be used as an antiaging agent for general polymers such as SBR, NBR, BR, IR, CR, EPDM, etc.

EXAMPLES

The examples and experiments will now be described. The following examples and experiments are for illustrative purposes only and not intended to limit the scope of this disclosure.

[Analysis and Evaluation Methods]

The products were analyzed by nuclear magnetic resonance (NMR) spectroscopy and gas chromatography-mass spectrometry (GC-MS). The reactants and products were quantitated by high-performance liquid chromatography (HPLC) under the following conditions.

All quantitation was performed at a wavelength of 254 nm. The eluent flow rate was 1 mL/min. Cosmosil 5C18-AR (4.6×150 mm, packed column) was used and the gradient elution condition is described in Table 1.

TABLE 1

Gradient elution condition (solvent composition)

| Time (min) | Solvent | |
|---|---|---|
| | Solvent A Distilled water (%) | Solvent B Acetonitrile (%) |
| 0 | 65 | 35 |
| 25 | 0 | 100 |
| 33 | 65 | 35 |

Pyrene was used as internal standard for quantitation of the products. Standard curve was drawn for each substance based on the pyrene area, and molar concentration of the product was calculated from the standard curve.

Preparation Examples

Preparation of 4,4'-DNDPA

Preparation Example 1

To a 3 reactor equipped with a cooler and a thermometer, 4-nitroaniline (4-NA, 138.2 g, 1 mol), sodium hydroxide (160 g, 4 mol) and DMSO (900 g) were added and the mixture was stirred. After adding nitrobenzene (369 g, 3 mol) dropwise and stirring for about 30 minutes, reaction was carried out at 70° C. while blowing oxygen. The proceeding of reaction was confirmed by HPLC. The yield of 4,4'-DNDPA was 95 mol % after 4 hours of reaction, and 98 mol % after 8 hours. After removing sodium hydroxide from the reaction mixture by filtering, the filtrate was concentrated by vacuum distillation at 70-80° C. and 10-20 mmHg to remove unreacted nitrobenzene and DMSO. Upon completion of the concentration, toluene (200 g) was added to the reactor while maintaining temperature at about 70° C. After stirring, water (250 g) was added while stirring. The product was solidified by cooling the reaction solution. The produced solid was separated by filtering and was washed with toluene. The recovered solid was further purified using toluene and water, and then dried.

Preparation Example 2

4,4'-DNDPA was prepared in the same manner as Preparation Example 1 except for changing reaction temperature as described in Table 2. The result is shown in Table 2.

TABLE 2

Table 2: Change in yield depending on reaction temperature

| Reaction temperature (° C.) | Reaction time (hr) | Yield of 4,4'-DNDPA (mol %) |
|---|---|---|
| 80 | 4 | 74 |
| 70 | 4 | 95 |
| 70 | 8 | 98 |
| 60 | 4 | 80 |
| 60 | 8 | 95 |
| 50 | 4 | 60 |
| 50 | 8 | 72 |

Preparation Example 3

4,4'-DNDPA was prepared in the same manner as Preparation Example 1 except for changing the kind and amount of the base as described in Table 3. The result is shown in Table 3.

TABLE 3

Change in yield depending on base

| Base | Amount of base g (mol) | Reaction time (hr) | Yield of 4,4'-DNDPA (mol %) |
|---|---|---|---|
| Potassium hydroxide | 224 (4) | 8 | 77 |
| Potassium t-butoxide* | 112.5 (1) | 8 | 62 |
| Tetramethylammonium hydroxide* | 215 (1.18) | 8 | 73 |
| Ethyl-α,β-bis(trimethylammonium hydroxide)/ tetramethylammonium hydroxide | 384 (1)/729 (2) | 8 | 94 |

*For potassium t-butoxide and tetramethylammonium hydroxide, 69.1 g (0.5 mol) of 4-NA was used.

Preparation Example 4

4,4'-DNDPA was prepared in the same manner as Preparation Example 1 except for changing the addition amount of the base as described in Table 4. The result is shown in Table 4.

TABLE 4

Change in yield depending on addition amount of base

| Amount of base g (mol) | Reaction time (hr) | Yield of 4,4'-DNDPA (mol %) |
|---|---|---|
| 80 (2) | 8 | 95 |
| 160 (4) | 8 | 98 |
| 240 (6) | 8 | 96 |
| 320 (8) | 8 | 93 |

Preparation Example 5

4,4'-DNDPA was prepared in the same manner as Preparation Example 1 except for changing the amount of nitrobenzene as described in Table 5. The result is shown in Table 5.

TABLE 5

Change in yield depending on amount of nitrobenzene

| Amount of nitrobenzene g (mol) | Reaction time (hr) | Yield of 4,4'-DNDPA (mol %) |
|---|---|---|
| 123 (1) | 8 | 75 |
| 246 (2) | 8 | 95 |

TABLE 5-continued

Change in yield depending on amount of nitrobenzene

| Amount of nitrobenzene g (mol) | Reaction time (hr) | Yield of 4,4'-DNDPA (mol %) |
|---|---|---|
| 369 (3) | 8 | 98 |
| 492 (4) | 8 | 96 |

Preparation Example 6

4,4'-DNDPA was prepared in the same manner as Preparation Example 1 except for changing the reaction atmosphere as described in Table 6. The result is shown in Table 6.

TABLE 6

Change in yield depending on amount of reaction atmosphere

| Reaction atmosphere | Reaction time (hr) | Yield of 4,4'-DNDPA (mol %) |
|---|---|---|
| Oxygen | 4 | 95 |
| Nitrogen | 4 | 76 |
| Air | 4 | 85 |

Examples

Preparation of 4,4'-BAADA

Example 1

The 4,4'-DNDPA (259 g, 1 mol) prepared in Preparation Example 1 was added to a high-pressure reactor. After adding methyl isobutyl ketone (MIBK, 500 g, 5 mol) as reactant and solvent and stirring, 3% Pt/C (10 g, water content=50%) was added as catalyst. Then, the inside of the reactor was purged with nitrogen 2 times. After injecting hydrogen into the reactor to a pressure of about 600 psi, the reaction temperature was raised to 160° C. Then, reaction was carried out at the reaction temperature for 3 hours while keeping the hydrogen pressure between 600 and 650 psi. Upon completion of the reaction, after lowering the temperature to 80° C. and discharging the remaining hydrogen gas, the catalyst was recovered by filtration.

The filtered reaction mixture was distilled to remove MIBK. 4,4'-Bis(1,3-dimethylbutylamino)diphenylamine (356 g) was obtained (yield: 97%, based on 4,4'-DNDPA).

Example 2

The 4,4'-DNDPA (259 g, 1 mol) prepared in Preparation Example 1 was added to a high-pressure reactor. After adding acetone (500 g, 8.6 mol) as reactant and solvent and stirring, 3% Pt/C (10 g, water content=50%) was added as catalyst. Then, the inside of the reactor was purged with nitrogen 2 times. After injecting hydrogen into the reactor to a pressure of about 600 psi, the reaction temperature was raised to 160° C. Then, reaction was carried out at the reaction temperature for 3 hours while keeping the hydrogen pressure between 600 and 650 psi. Upon completion of the reaction, after lowering the temperature to 80° C. and discharging the remaining hydrogen gas, the catalyst was recovered by filtration.

The filtered reaction mixture was distilled to remove acetone. 4,4'-Bis(isopropylamino)diphenylamine (272 g) was obtained (yield: 96%, based on 4,4'-DNDPA).

Example 3

The 4,4'-DNDPA (259 g, 1 mol) prepared in Preparation Example 1 was added to a high-pressure reactor. After adding cyclohexanone (500 g, 5.1 mol) as reactant and solvent and stirring, 3% Pt/C (10 g, water content=50%) was added as catalyst. Then, the inside of the reactor was purged with nitrogen 2 times. After injecting hydrogen into the reactor to a pressure of about 600 psi, the reaction temperature was raised to 160° C. Then, reaction was carried out at the reaction temperature for 3 hours while keeping the hydrogen pressure between 600 and 650 psi. Upon completion of the reaction, after lowering the temperature to 80° C. and discharging the remaining hydrogen gas, the catalyst was recovered by filtration.

The filtered reaction mixture was distilled to remove cyclohexanone. 4,4'-Bis(cyclohexylamino)diphenylamine (341 g) was obtained (yield: 94%, based on 4,4'-DNDPA).

Example 4

The 4,4'-DNDPA (259 g, 1 mol) prepared in Preparation Example 1 was added to a high-pressure reactor. After adding MIBK (250 g, 2.5 mol) and acetone (250 g, 4.3 mol) as reactant and solvent and stirring, 3% Pt/C (10 g, water content=50%) was added as catalyst. Then, the inside of the reactor was purged with nitrogen 2 times. After injecting hydrogen into the reactor to a pressure of about 600 psi, the reaction temperature was raised to 160° C. Then, reaction was carried out at the reaction temperature for 3 hours while keeping the hydrogen pressure between 600 and 650 psi. Upon completion of the reaction, after lowering the temperature to 80° C. and discharging the remaining hydrogen gas, the catalyst was recovered by filtration.

The filtered reaction mixture was distilled to remove acetone and MIBK. A mixture (308 g) of 4-(isopropylamino)-4'-(1,3-dimethylbutylamino)diphenylamine, 4,4'-bis(isopropylamino)diphenylamine and 4,4'-bis(1,3-dimethylbutylamino)diphenylamine was obtained (yield: 95%, based on 4,4'-DNDPA).

The present invention allows selective preparation of 4,4'-DNDPA without byproducts using inexpensive raw materials and bases and thus allows preparation of 4,4'-BAADA via a simplified process and in high yield through a direct reaction with a ketone without passing the intermediate 4,4'-DADPA.

The present invention has been described in detail with reference to specific embodiments thereof. However, it will be appreciated by those skilled in the art that various changes and modifications may be made in these embodiments without departing from the principles and spirit of the disclosure, the scope of which is defined in the appended claims and their equivalents.

What is claimed is:

1. A method for preparing 4,4'-dinitrodiphenylamine comprising reacting 4-nitroaniline with nitrobenzene in a polar organic solvent in the presence of a base catalyst complex, wherein the base catalyst complex comprises tetramethylammonium hydroxide (TMAH) and ethyl-α,β-bis(trimethylammonium hydroxide).

2. The method for preparing 4,4'-dinitrodiphenylamine according to claim 1, wherein the polar organic solvent is dimethyl sulfoxide, dimethylformamide, N-methylpyrrolidinone or a mixture thereof.

3. The method for preparing 4,4'-dinitrodiphenylamine according to claim 1, wherein the base catalyst complex further comprises one or more species selected from the group consisting of sodium hydroxide (NaOH), potassium hydroxide (KOH) and potassium t-butoxide (t-BuOK).

4. The method for preparing 4,4'-dinitrodiphenylamine according to claim 1, wherein the 4-nitroaniline and the nitrobenzene are used at a molar ratio 1:1-16.

5. The method for preparing 4,4'-dinitrodiphenylamine according to claim 1, wherein the 4-nitroaniline and the base are used at a molar ratio 1:1-20.

6. The method for preparing 4,4'-dinitrodiphenylamine according to claim 1, wherein the polar organic solvent is used in an amount of 1-50 parts by volume per 1 part of the reactants (4-nitroaniline and nitrobenzene) by volume.

7. The method for preparing 4,4'-dinitrodiphenylamine according to claim 1, wherein the reaction is performed at 20-100° C.

8. The method for preparing 4,4'-dinitrodiphenylamine according to claim 1, wherein the reaction is performed under oxygen, air or nitrogen atmosphere.

9. A method for preparing 4,4'-bis(alkylamino)diphenylamine (the alkyl is $C_1$-$C_{18}$ alkyl) comprising:
reacting 4-nitroaniline with nitrobenzene in a polar organic solvent in the presence of a base catalyst complex to prepare 4,4'-dinitrodiphenylamine, wherein the base catalyst complex comprises tetramethylammonium hydroxide (TMAH) and ethyl-α,β-(trimethylammonium hydroxide); and
hydrogenating the resulting 4,4'-dinitrodiphenylamine with a ketone compound in the presence of a hydrogenation catalyst to prepare 4,4'-bis(alkylamino)diphenylamine.

10. The method for preparing 4,4'-bis(alkylamino)diphenylamine according to claim 9, wherein the base catalyst complex further comprises one or more species selected from the group consisting of sodium hydroxide (NaOH), potassium hydroxide (KOH) and potassium t-butoxide (t-BuOK).

11. The method for preparing 4,4'-bis(alkylamino)diphenylamine according to claim 10, wherein the ketone compound is a $C_1$-$C_{10}$ alkylketone compound or a $C_1$-$C_{10}$ cycloalkylketone compound.

12. The method for preparing 4,4'-bis(alkylamino)diphenylamine according to claim 11, wherein the $C_1$-$C_{10}$ alkylketone compound is selected from acetone, methyl isobutyl ketone, methyl isoamyl ketone, methyl ethyl ketone and methyl n-butyl ketone, and the $C_1$-$C_{10}$ cycloalkylketone compound is selected from cyclohexanone and methyl cyclohexyl ketone.

13. The method for preparing 4,4'-bis(alkylamino)diphenylamine according to claim 9, wherein the ketone compound is used in an amount of 3-10 mol per 1 mol of 4,4'-dinitrodiphenylamine.

14. The method for preparing 4,4'-bis(alkylamino)diphenylamine according to claim 9, wherein the hydrogenation catalyst is a precious metal catalyst, a reduction catalyst, or a carbon-supported precious metal catalyst.

15. The method for preparing 4,4'-bis(alkylamino)diphenylamine according to claim 14, wherein the precious metal catalyst is selected from Pd and Pt, the reduction catalyst is selected from Ni—Fe—Al, Cu—Cr and Raney Ni, and the carbon-supported precious metal catalyst is selected from Pt/C and Pd/C.

16. The method for preparing 4,4'-bis(alkylamino)diphenylamine according to claim 9, wherein the hydrogenation catalyst is used in an amount of 0.05-0.2 part by weight per 1 part of the 4,4'-dinitrodiphenylamine by weight.

17. The method for preparing 4,4'-bis(alkylamino)diphenylamine according to claim 9, wherein the hydrogenation is performed at 50-200° C. and at a hydrogen pressure of 300-1000 psi.

18. The method for preparing 4,4'-bis(alkylamino)diphenylamine according to claim 9, wherein the 4,4'-dinitrodiphenylamine and the ketone compound are used at a molar ratio 1:3-10.

* * * * *